US009142061B2

(12) United States Patent
Metaxas (10) Patent No.: US 9,142,061 B2
(45) Date of Patent: Sep. 22, 2015

(54) FLUID FLOW ANALYSIS FOR CARDIOVASCULAR DIAGNOSTICS

(75) Inventor: Dimitri Metaxas, Princeton, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 441 days.

(21) Appl. No.: 13/359,188

(22) Filed: Jan. 26, 2012

(65) Prior Publication Data
US 2012/0215510 A1    Aug. 23, 2012

Related U.S. Application Data

(60) Provisional application No. 61/436,271, filed on Jan. 26, 2011.

(51) Int. Cl.
| | | |
|---|---|---|
| G06K 9/00 | (2006.01) | |
| G06T 17/20 | (2006.01) | |
| G06T 13/20 | (2011.01) | |
| G06F 19/00 | (2011.01) | |

(52) U.S. Cl.
CPC ............... G06T 17/205 (2013.01); G06T 13/20 (2013.01); *G06F 19/321* (2013.01); *G06F 19/3437* (2013.01); *G06T 2210/24* (2013.01)

(58) Field of Classification Search
CPC ... G06F 19/321; G06F 19/3437; G06T 13/20; G06T 17/205; G06T 2210/24
USPC .................................. 382/128, 131, 132, 154
See application file for complete search history.

(56) References Cited

U.S. PATENT DOCUMENTS

| | | | | |
|---|---|---|---|---|
| 6,987,511 | B2* | 1/2006 | Taubin .......................... | 345/420 |
| 8,031,919 | B2* | 10/2011 | Eskildsen et al. ............. | 382/128 |
| 8,189,885 | B2* | 5/2012 | Saha et al. .................... | 382/128 |
| 8,682,626 | B2* | 3/2014 | Ionasec et al. ................. | 703/6 |

OTHER PUBLICATIONS

"Patient-specific modeling of left heart anatomy, dynamics and hemodynamics from high resolution 4D CT" Mihalef, V.; Ionasec, R.; Yang Wang; Yefeng Zheng; Georgescu, B.; Comaniciu, D. Biomedical Imaging: From Nano to Macro, 2010 IEEE International Symposium on DOI: 10.1109/ISBI.2010.5490298 Publication Year: 2010, pp. 504-507.*
Jones et al, "Patient-specific analysis of left ventricular blood flow", Proceeding of MICCAI '98, Springer LNCS, 1998, pp. 156-166.
Mihalef et al, "Textured liquids based on the marker level set", EUROGRAPHICS (2007), vol. 26, No. 3, pp. 457-466.
Mihalef et al, "Interaction of multiphase flow with animated models", Graphical Models (2007), 70, 3, pp. 33-42.

(Continued)

*Primary Examiner* — Tom Y Lu
(74) *Attorney, Agent, or Firm* — Stephen H. Eland; Dann, Dorfman, Herrell & Skillman (57) ABSTRACT

This invention presents a method to simulate how blood flows through the heart, using the reconstructed 4D motion of the endocardial surface of the left ventricle. The reconstruction, utilizing a computing device, captures the motion of the full 3D surfaces of the complex features, such as the papillary muscles and the ventricular trabeculae. By visualizing the flow field, the capability of viewing the interactions between the blood and the trabeculae in far more detail has been achieved.

21 Claims, 8 Drawing Sheets

(56) References Cited

OTHER PUBLICATIONS

Mihalef et al, "Atrioventricular blood flow simulation based on patient-specific data." Functional Imaging and modeling of the heart. Springer Berlin Heidelberg, 2009. pp. 386-395.

Mihalef et al, "Patient-specific modeling of left heart anatomy, dynamics and hemodynamics from high resolution 4D CT." Biomedical Imaging: From Nano to Macro, 2010 IEEE International Symposium on. IEEE, 2010.

Shen et al, "Adaptive-focus statistical shape model for segmentation of 3D MR structures." Medical Image Computing and Computer-Assisted Intervention—MICCAI 2000. Springer Berlin Heidelberg, 2000.

Shen et al, "Active volume models for 3D medical image segmentation." Computer Vision and Pattern Recognition, 2009. CVPR 2009. IEEE Conference on. IEEE, 2009.

Sussman et al, "A parallelized, adaptive algorithm for multiphase flows in general geometries." Computers & structures 83.6 (2005): 435-444.

Zheng et al, "Four-chamber heart modeling and automatic segmentation for 3-D cardiac CT volumes using marginal space learning and steerable features." Medical Imaging, IEEE Transactions on 27.11 (2008): 1668-1681.

Zhu et al, "Region competition: Unifying snakes, region growing, and Bayes/MDL for multiband image segmentation." Pattern Analysis and Machine Intelligence, IEEE Transactions on 18.9 (1996): 884-900.

Chen, et al. "3D Cardiac Anatomy Reconstruction Using High Resolution CT Data", MICCAI 2004, LNCS 3216, pp. 411-418.

De Zelicourt, et al. "Flow Simulations in Arbitrarily Complex Cardiovascular Anatomies—An Unstructured Cartesian Grid Approach", Computers & Fluids 38, 2009, pp. 1749-1762.

Yokoi, et al, "Three Dimensional Numerical Simulation of Flows With Complex Geometries in a Regular Cartesian Grid and Its Application to Blood Flow in Cerebral Artery With Multiple Aneurysms", Journal of Computational Physics 202, 2005, pp. 1-19.

\* cited by examiner

FLUID FLOW ANALYSIS FOR CARDIOVASCULAR DIAGNOSTICS

PRIORITY CLAIM

The present application claims priority under 35 U.S.C. §119 to U.S. Provisional Patent Application No. 61/436,271 filed on Jan. 26, 2011. The entire disclosure of the foregoing application is incorporated herein by reference.

FIELD OF THE INVENTION

The present invention relates to the field of computer simulation of mammalian biological system. More specifically, the present invention relates to computer modeling of human patient system and fluid flow through the systems. In particular, the present invention relates to simulation of blood flow through a computer model of a patient's heart.

BACKGROUND OF THE INVENTION

Following a heart attack or the development of some cardiovascular diseases, the movement of the heart walls during the cardiac cycle may change, which affects the motion of blood through the heart. Currently, valvular blood flow can be monitored using imaging techniques such as Doppler ultrasound and MRI. However, because the spatial resolution of such techniques are low, and it is not possible to observe the detailed interaction of blood flow and the endo-cardial surface of the heart, the formation of a cardiac thrombus remains difficult to predict. If a physician were able to visualize or quantitatively measure the detailed alteration of the blood flow by altered contraction, he/she might be able to make a better diagnosis or treatment plan.

Heart model reconstruction is essential to the simulation results. The detailed cardiac shape features, which are accurately reconstructed from these images can be used as the boundary conditions for a fluid simulator to derive the hemodynamics along the whole heart cycle.

With the rapid development of high-resolution cardiac CT, patient-specific blood flow simulation is quickly becoming one of the central goals in the study of cardiac blood flow. Mihalef et al. (2009) published a framework for simulating atrioventricular blood flow, and showed simulation results using a complete model of the left side of the heart, including the atrial venae and an aortic stub, together with modeled valve kinematics. The geometry used in Mihalef et al. (2009) was obtained from scans based on data from the Visible Human Project, while the kinematics was transferred to the model from MRI data. Later, Mihalef et al. (2010) used smoothed 4D CT data to simulate left ventricular blood flow, and compared the flow around through the aortic valve in a healthy heart and two diseased hearts. The models derived from CT data in Mihalef et al. (2010) were highly smoothed and were not useful for understanding the true interactions between the blood flow and the walls.

Earlier work in blood flow simulation used less refined models. For example, Jones and Metaxas (1998) were the first to extract boundaries from MRI data to perform patient-specific blood flow simulations. Later, Q. Long et al. (2003) and Saber N. (2003) used simple models of the left side of the heart, with smooth ventricular walls, and imposed boundary conditions in the valve regions.

There has also been work on the 3D cardiac reconstruction from CT images Zheng et al. (2008); von Berg and Lorenz (2005); Lorenz and von Berg (2006). However, despite the higher level of structural detail potentially available in CT data, most prior work has not sought to capture the finer detail structures of the myocardium, such as the papillary muscles and the trabeculae. The conventional approach to reconstructing cardiac structures from 3D images (e.g., for generating generic or patient-specific models of the heart) is a model-based one that uses a smooth parametric model to guide the segmentation of cardiac structures from the 3D images. Such parametric models capture the overall shape of the heart wall, but are too coarse to capture or incorporate many of the finer scale anatomical features. Recent advances in CT technology have made the acquisition of higher resolution cardiac images possible, which can capture previously unseen cardiac structure details. Chen et al. proposed a hybrid framework for 3D cardiac reconstruction [Chen et al. 2004]. That method has provided high resolution segmentation results of the complex cardiac structure. Their results captured the papillary muscles and detail structure of the myocardium.

The described invention uses a high resolution heart model by using segmenting higher-quality CT scans of normal subjects and live patients with cardiovascular disease that allow the capture of the complex details of the heart walls and trabeculae. The approach, which estimates the predefined motion for the valves, whose asynchronous opening and closing provides a simple geometric mechanism for taking care of those boundary conditions, relies on the reasonable assumption that the left ventricle drives essentially all of the dynamics of the blood flow in the left side of the heart. The described invention captures the fine detail structures of the myocardium, as well as the one-to-one correspondence between frames, which is required in the blood simulator. With the one-to-one correspondence, one can do interpolation among different time frames to get a smoother heart cycle reconstruction.

SUMMARY OF INVENTION

In light of the foregoing, the present invention provides an improved system for producing a simulation of blood flow in a heart of a patient.

According to one aspect of the invention, a computed tomography image of a patient's anatomical system is created. The anatomical system may be a patient's heart. A mesh of the computed tomography image may be decimated, allowing collapse of one vertex into one of its neighbors. The mesh is then smoothed to preserve details. In one embodiment, the smoothing is restricted to a tangential direction. After the step of smoothing, the method may include the step of remeshing a triangular mesh with an incremental isotropic technique. A simulation may then be produced of the fluid flow through the anatomical system. For instance, the simulation may be the blood flow through the heart.

According to another aspect, the present invention comprises a computing device programmed to perform the steps of the method described above.

According to yet another aspect, the present invention provides a method for measuring artherosclerotic plaques with improved resolution;

According to another aspect, the present invention provides a method for creating time series of heart imaging.

According to yet another aspect, the present invention provides a method for providing movement statistics of normal heart beat per cardiac segment According to still another aspect, the present invention provides a method for creating a computer simulation of a patient's heart comprising the steps of building a patient specific computed tomography image including details of the trabeculae of the heart. The flow of the blood through the heart during the cardiac cycle is then simulated based on the computed tomography image, wherein the simulation illustrates the blood flow within the trabeculae.

DESCRIPTION OF THE DRAWINGS

The foregoing summary as well as the following detailed description of the preferred embodiment of the present invention will be better understood when read in conjunction with the appended drawings, in which.

DETAILED DESCRIPTION OF THE INVENTION

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

Heart Model Reconstruction

Heart models are reconstructed using a deformable model method. A semi-automatic segmentation is used to get the initial segmentation from high resolution CT data for an initial (3D) frame of data. This semi-automatic segmentation can be time consuming and tedious, so it may not be efficient to use it for segmentation of all the frames. The initial high resolution mesh model is generated, e.g., by a computing device programmed to perform this method by instructions stored on a tangible machine readable medium (herein "a computing device"), as an isosurface of the segmentation. Geometric processing on a computing device is then applied to the initial model to get a smooth and regular mesh with an appropriate number of vertices. Based on the initial model from one time frame, the described method, utilizing a computing device, deforms it towards the boundaries on the other frames. During formation, the topology of the model is kept unchanged. One-to-one correspondence between frames, as a requirement for the fluid simulator in later processes also can be obtained. These novel and powerful methods, utilizing a computing device, can extract the full 3D surfaces of these complex anatomical structures. The results have been validated based on the ground truth segmented by multiple clinical experts. Valves can be difficult to capture in CT images such that valve models may be added to the heart meshes, utilizing a computing device, in the sequence.

CT Data Acquisition

The CT images were acquired on a 320-MSCT scanner (Toshiba Aquilion ONE, Toshiba Medical Systems Corporation). This advanced diagnostic imaging system is a dynamic volume CT scanner that captures a whole-heart scan in a single rotation, and achieves an isotropic 0.5 mm volumetric resolution with less motion artifact than the conventional 64-MSCT scanners. A conventional contrast enhanced CT angiography protocol was adapted to acquire the CT data in this work. After the intravenous injection of the contrast agent, the 3D+ time CT data were acquired in a single heart beat cycle when the contrast agent was circulated to the left ventricle and aorta, so that it was able to achieve an optimal intensity difference level between the blood pool and the left ventricular myocardium. After acquisition, 3D images were reconstructed at 10 time phases in between the R-to-R waves using ECG gating implemented on a computing device. The acquired isotropic data had an in-plane dimension of 512 by 512 pixels, with an effective atrio-ventricular region measuring about 300 pixels.

Reconstruction Framework

The heart model reconstruction framework includes: initial model construction, deformable model based segmentation, valve reconstruction and attachment and interpolation between time frames al performed utilizing a computing device.

Initial Model Construction

Utilizing a computing device, throughout, the initial model is generated using snake-based segmentation on one time frame of the CT image. A semi-automatic segmentation method was used to get the initial model. Once this model is generated, it is used to segment the rest of other frames automatically.

Isosurface detection is applied to generate the model mesh from the first segmented result. However, the resulting mesh may be bulky, noisy and irregular. To get a better initialization model, some geometric processing may be done on that mesh, such as decimating, detail-preserving smoothing and isotropic remeshing. Such geometric processing, which leads to high-quality meshes, is desirable for subsequent model deformation. Again, these functions are performed on a computing device.

The initial model may be too large to readily modify, so in the present instance the mesh was decimated to an appropriate size, utilizing a computing device. The desirable number of vertices is given as a constraint. Edge collapses, which simply collapse one vertex into one of its neighbors, may be performed during decimation. Some error metrics may be used to decide the priority of the edge collapses. Finally, a mesh with much fewer vertices, but that still retains most of the shape details was obtained. Meshes that have been decimated to about 20,000 vertices are complex enough to capture the fine details of the heart.

Detail-preserving smoothing is performed after decimation, utilizing a computing device. In the present instance, the smoothing is restricted to the tangential direction. Instead of moving each vertex towards the centroid of its neighbors, which would smooth out the shape details and sharp features, detail-preserving smoothing ensures higher quality meshes without losing details.

Isotropic remeshing may improve the mesh quality. In irregular meshes, the vertices with high valences exert strong internal forces to drag other vertices, which can cause unrealistic results in deformable models. Utilizing a computing device, an incremental isotropic remeshing technique is used to remesh the given triangular mesh so that all edges have approximately the same target edge length and the triangles are as regular as possible. Using the described method, the target edge length is set to be the mean of the current edge lengths. Edge length thresholds are set around the target edge length. During the incremental isotropic remeshing process, edges longer than the higher edge bound are split until all edges are shorter than the threshold; shorter edges are collapsed if collapsing does not result in new edges longer than the higher threshold; edges are flipped to equal valences; vertices are moved to new positions to get regular triangle meshes; and finally vertices are projected back to the original surfaces to keep the shape unchanged. This process generally is iterated several times to get the final results.

Deformable Model Based Segmentation

To get the segmentation of the rest frames as well as one-to-one correspondence between frames, one would define using a computing device an energy function, including an external energy, derived from the image so that it is smaller at the boundaries, and a model energy, which reflects the differences between the original model and the deformed model. By minimizing the energy function, it drags the model towards the boundaries and keeps the shape of the model unchanged during deformation as performed on a computing device.

Given a gray level image $I(x, y)$, viewed as a function of continuous position variables $(x, y)$, the model $M_{t-1}$ derived from the previous frame is used to fit the current frame $M_t$. The energy function to be minimized is defined as follows:

$$E(M_t, I_t, M_{t-1}) = E_{ext}(M_t, I_t) + E_{model}(M_t, M_{t-1}). \quad (1)$$

The external energy $E_{ext}$ is designed to move the deformable model towards object boundaries.

$$E_{ext}(M_t, I_t) = -E_{ext}(M_t, I_t) = -|\nabla I|^2 \quad (2)$$

where $\nabla$ is the gradient operator.

The model energy is defined as the differences of vertex normals and attribute vectors. An attribute vector is attached to each vertex of the model, which reflects the geometric structure of the model from a local to global level. In 3D, for a particular vertex Vi, each attribute is defined as the volume of a tetrahedron on that vertex. The other three vertices form the tetrahedron are randomly chosen from the lth level neighborhood of $V_i$. Smaller tetrahedrons reflect the local structure near a vertex while larger tetrahedrons reflect a more global information around a vertex. The attribute vector, if sufficient enough, uniquely characterizes different parts of a surface of a boundary.

The volume of a tetrahedron is defined as $f_t(V_i)$. The attribute vector on a vertex is defined as.

$$F(V_i) = [f_1(V_i), f_2(V_i), \ldots, f_{R(V_i)}(V_i)] \quad (3)$$

where $R(V_i)$ is the neighborhood layers we want to use around $V_i$.

As elaborated earlier, the model energy term reflects the differences of vertex normals and attribute vectors between the original model and the deformed model.

$$E_{model}(M_t, M_{t-1}) = \sum_{i=1}^{N}\left(\alpha(n_{t,i} - n_{t-1,i})^2 + \sum_{l=1}^{R(V_i)}\delta_l(f_{t,l}(V_i) - f_{t-1,l}(V_i))^2\right), \quad (4)$$

where $f_{t,l}(V_i)$ and $f_{t-1,l}(V_i)$ are components of attribute vectors of the model and deformed model at vertex $V_i$, respectively. $\alpha$ determines the importance of the vertex normals compared to the attribute vectors. $\delta_l$ here denotes the importance of the l th neighborhood layers. $R(V_i)$ is the number of neighborhood layers around vertex $V_i$.

A greedy algorithm is used here to minimize the energy function. The proposed algorithm is iterative. During each iteration, the first step is to minimize the external energy, moving vertices towards the minimum gradient of the image; the second step is to minimize the model energy; a neighborhood of a vertex has been examined and the point in the neighborhood with the minimum model energy would be chosen as the new location of the vertex. The iterations continue until the energy converges. While this greedy algorithm might fall into a local minimum, the experiments show satisfactory results.

During the deformation, we suggest moving a surface segment as a whole, rather than a single vertex. This would avoid the risk of getting trapped in a local minimum, and also speed up the convergence. Let $V_i$ be the vertex to be deformed during a particular iteration. The first to $R(V_i)$th neighborhood layers are about to move together as a surface segment. Suppose $V_i$ is to move to $V_i + \Delta$ as a tentative position. Then the new position of each vertex $nbr_{l,m}(V_i)$, the mth vertex on the l th neighborhood layer, is set to move to $$nbr_{l,m}(V_i) + \Delta \cdot \exp\left(-\frac{l^2}{2\delta^2}\right), \quad (5)$$

where $\delta$ is a parameter determining the locality of the transformation. We make the transformation unchanged on the boundary of the surface segment, such that the continuity has been maintained.

The parameter $R(V_i)$ that determines the locality if the deformation is chosen to be large in the initial iteration, and is then gradually reduced to 1. Therefore, initially there are more vertices involved in the deformation. More global features are used in deformation. In later stages, more local deformations are performed.

The motion of an incompressible fluid is governed by the laws of conservation of momentum and mass. These two laws are modeled by the Navier-Stokes equations:

$$\rho\left(\frac{\partial u}{\partial L} + u \cdot \nabla u\right) = -\nabla P + \mu \nabla^2 u$$

$$\nabla \cdot u = 0$$

The first equation enforces conservation of momentum. Here, ρ is the fluid density, u is the 3D velocity vector field, P is the scalar pressure field, and μ is the coefficient of viscosity. The second equation states that the divergence of velocity is zero everywhere, and thus there are no sources or sinks anywhere in the flow, conserving mass.

The Navier-Stokes equations for graphics applications may be solved utilizing a computing device by applying a staggered grid across the domain and explicitly solving for the three components of velocity at the cell faces. Successive over-relaxation may then be used to solve for pressure and correct the velocities to maintain incompressibility.

Our fluid-solid interaction system uses a "boundary immersed in a Cartesian grid formulation", which allows an easy treatment of complex geometries embedded in the computational domain, utilizing a computing device, especially advantageous when dealing with moving boundaries.

The 3D mesh is generated from CT data is represented by a marker level set ("MLS"). Here, markers are placed on the boundary, and are used to correct the level set at every time step. The marker level set approach is similar to the particle level set method, but since markers are only placed only on the surface, MLS has been proven to be more efficient and significantly more accurate for complex boundaries. Additionally, utilizing a computing device, our specific solver achieves efficiency by implementing a parallel and adaptive mesh refinement approach.

Utilizing a computing device, the heart models used here are embedded in a computational mesh of $100^3$ cells on which the full Navier-Stokes equations with a viscous component are solved using finite difference method. The blood is modeled as a Newtonian fluid, with viscosity set at 4 mPa·s and density set at 1060 kg/m$^3$, which are physiologically accepted values for a normal patient. The heart geometric model is fed to the solver as a discrete set of meshes with point correspondences, which allow easy temporal interpolation and also obtaining the velocity of the heart mesh at every point in time. The heart mesh and its velocity are rasterized onto the Eulerian grid as a marker level set, respectively as an Eulerian velocity (subsequently extrapolated onto a MAC grid). The marker level set and the velocity are used to impose the appropriate boundary conditions to the fluid solver. A simulation of two complete cardiac cycles takes about four days on a machine with a Core 2 Quad processor and 8 GB of RAM.

Visualization

The framework was adapted to perform the fluid simulation. With the fluid velocity fields and level sets generated for each time step, Paraview is used to visualize the simulations. On a machine with a Core 2 Quad processor and 8 GB of RAM, each of the visualizations may take 30 minutes to render 83 frames. A healthy heart was analyzed and is described below.

Figure 5:
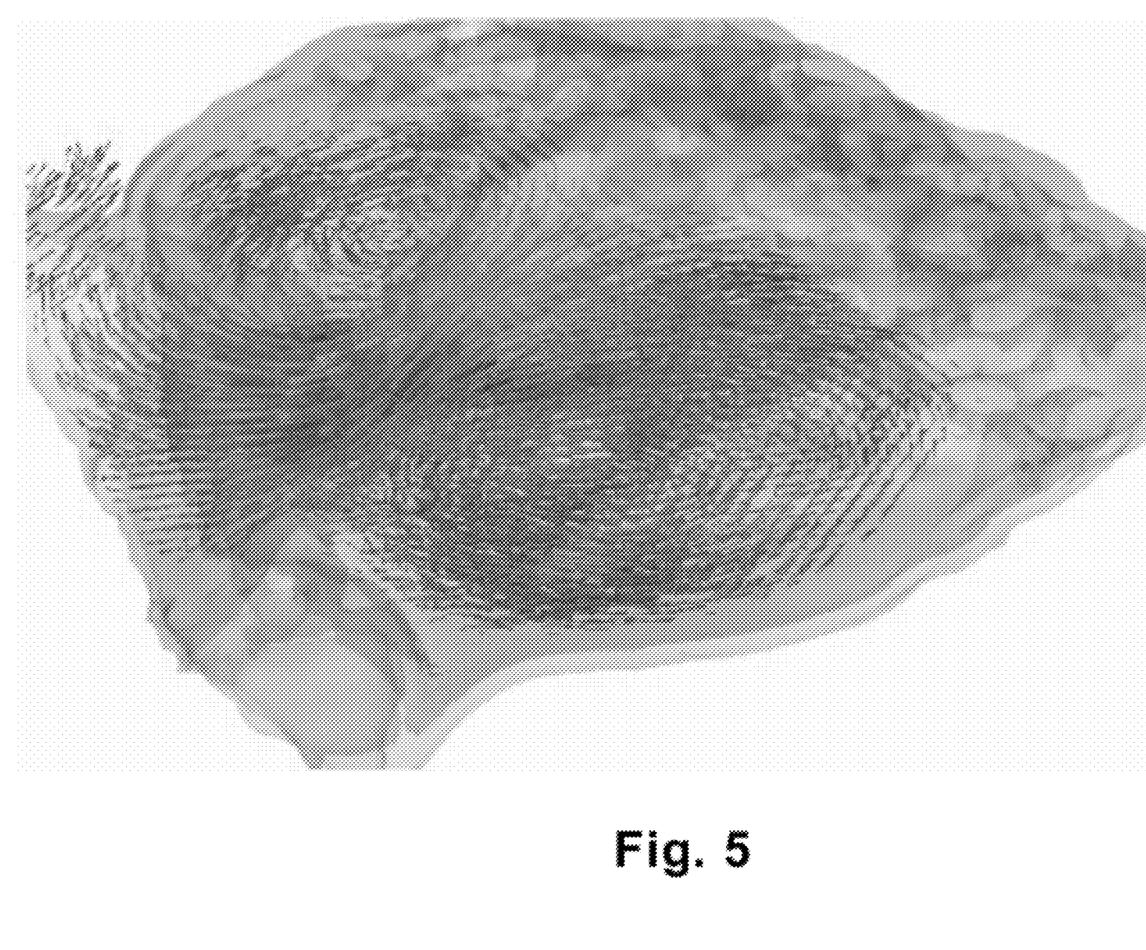
FIG. 5 illustrates the blood flow from outside heart during diastole resulting from modeling of fluid flow through the model of the heart illustrated in FIG. 3.

A visualization of the velocity field of the entire heart was performed, as seen in FIG. 5. The velocity of the blood at a given point is represented by a cone pointed in the direction of the flow. A cone's size increases linearly as the magnitude of the velocity increases. Additionally, we adjust the color of a cone by first setting its hue to 160 (blue), and then linearly lowering this value to a minimum of 0 (red) as velocity increases.

Cross-sections of the heart were examined and velocities were visualized in order to have a clearer picture of how each of the structures and trabeculae affect the flow of blood. The velocity field was visualized in the same way as above. The velocity at each point was represented with a colored cone. The flow field is plotted very close to the heart surface, so that the visualization further away does not obstruct the view of the trabeculae. Screenshots of this visualization can be seen in FIG. 6.

Figure 1:
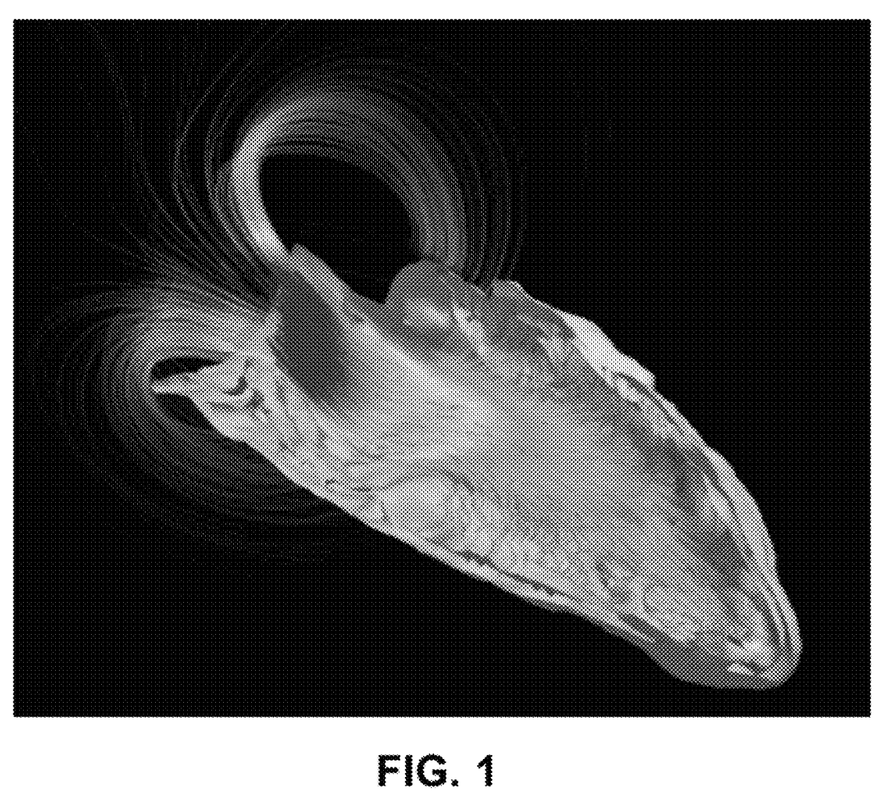
FIG. 1 illustrates the streamlines of cardiac blood flow resulting from modeling of fluid flow through a heart during diastole.
Figure 2:
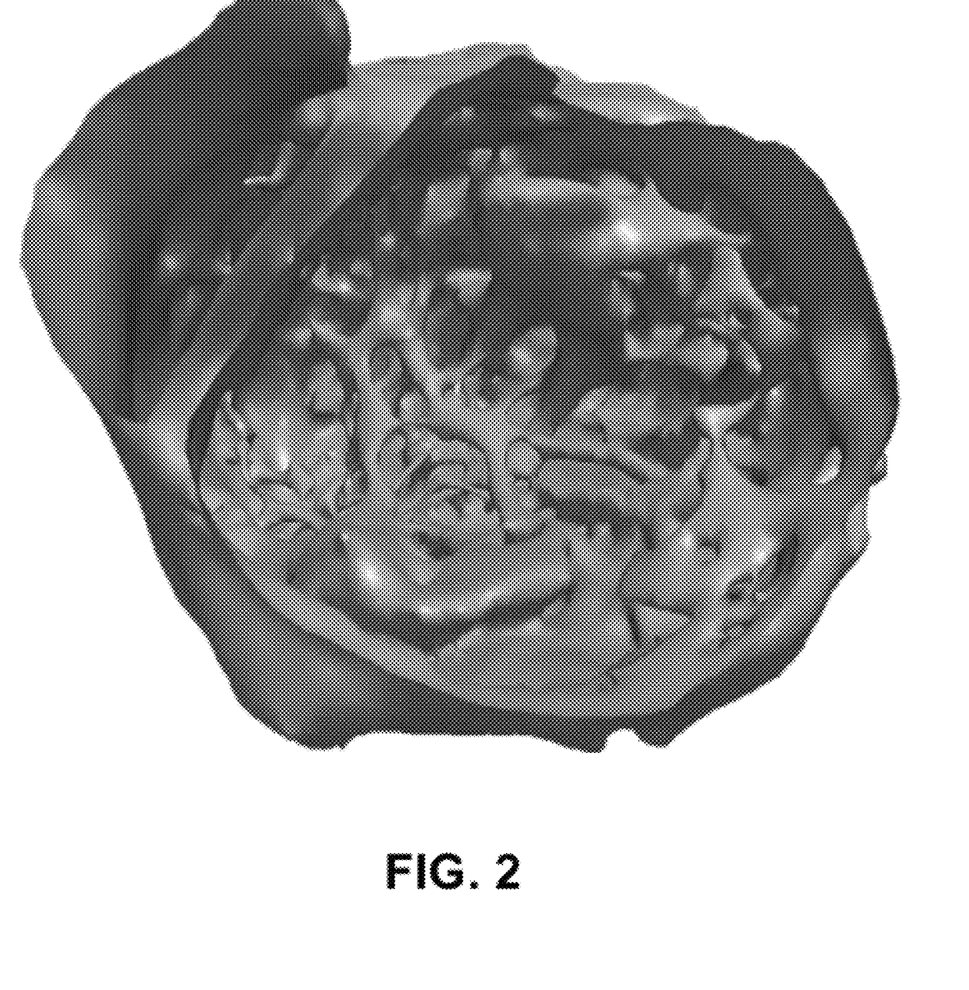
FIG. 2 illustrates a mesh model of a heart reconstructed from CT data in which the heart valves are removed.
Figure 3:
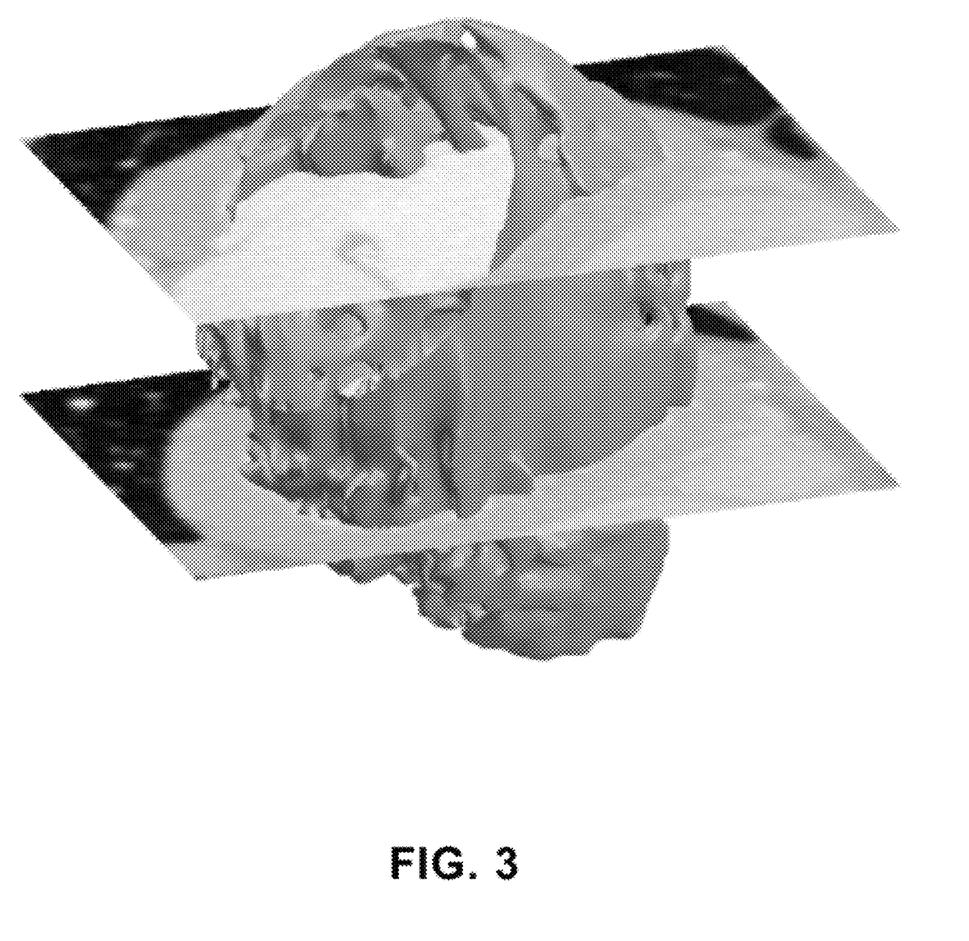
FIG. 3 illustrates a mesh model of a heart extracted from CT data after isosurfacing and geometry processing.
Figure 4A:
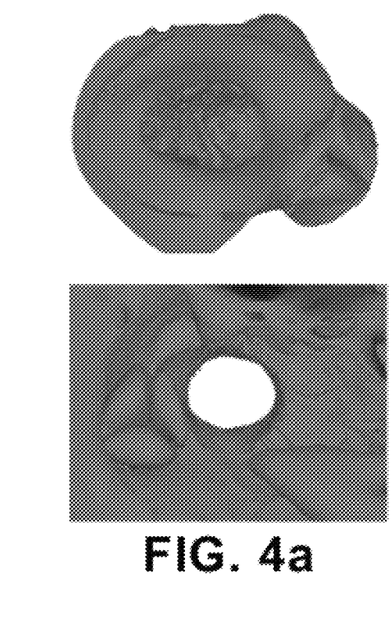
FIG. 4a illustrates outside and inside views of the valves of the mesh model of the heart illustrated in FIG. 3 at a beginning stage of the cardiac cycle in which the mitral valve is open.
Figure 4B:
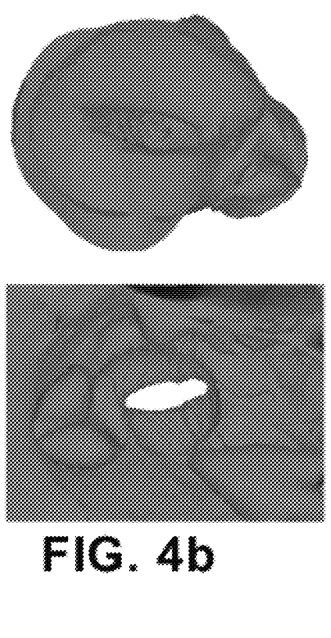
FIG. 4b illustrates outside and inside views of the valves of the mesh model of the heart illustrated in FIG. 3 at a stage of the cardiac cycle subsequent to the stage illustrated in FIG. 4a after the mitral valve has begun to close.
Figure 4C:
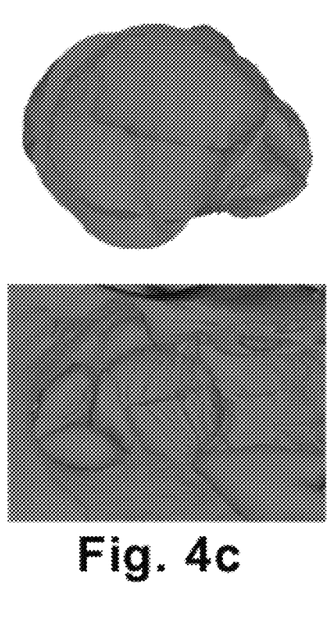
FIG. 4c illustrates outside and inside views of the valves of the mesh model of the heart illustrated in FIG. 3 at a stage of the cardiac cycle subsequent to the stage illustrated in FIG. 4b after the mitral valve has closed.
Figure 4D:
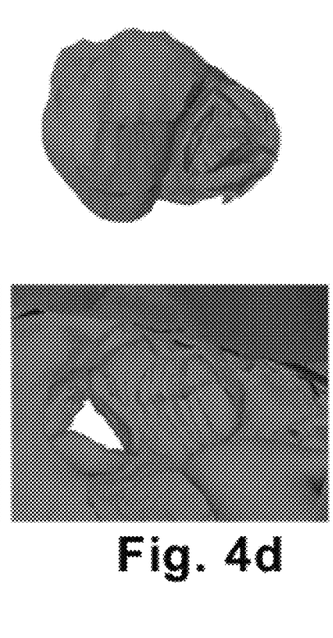
FIG. 4d illustrates outside and inside views of the valves of the mesh model of the heart illustrated in FIG. 3 at a stage of the cardiac cycle subsequent to the stage illustrated in FIG. 4c wherein the mitral valve is closed and the aortic valve has opened.
Figure 7:
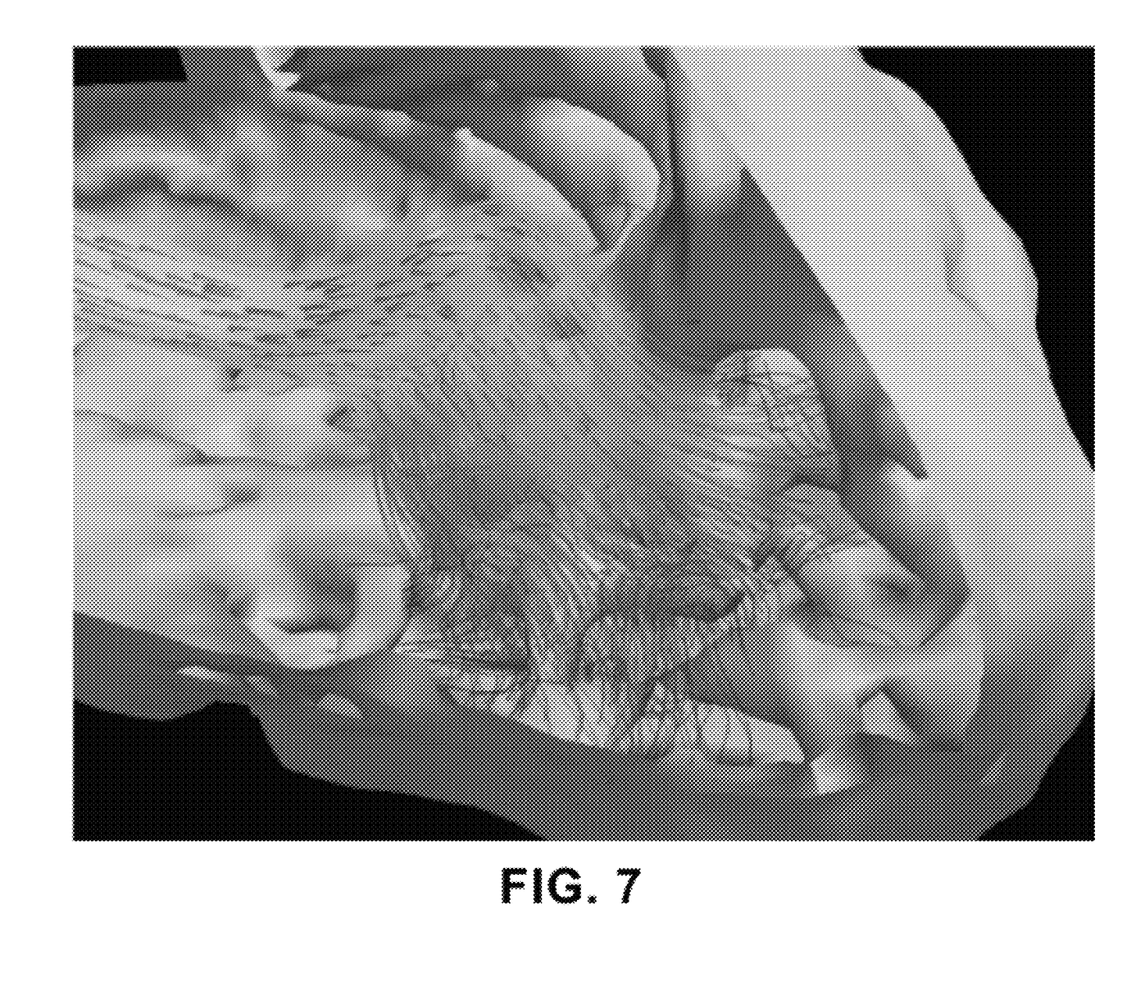
FIG. 7 illustrates the blood flow streamlines during diastole resulting from modeling of fluid flow through the model of the heart illustrated in FIG. 3.
Figure 8:
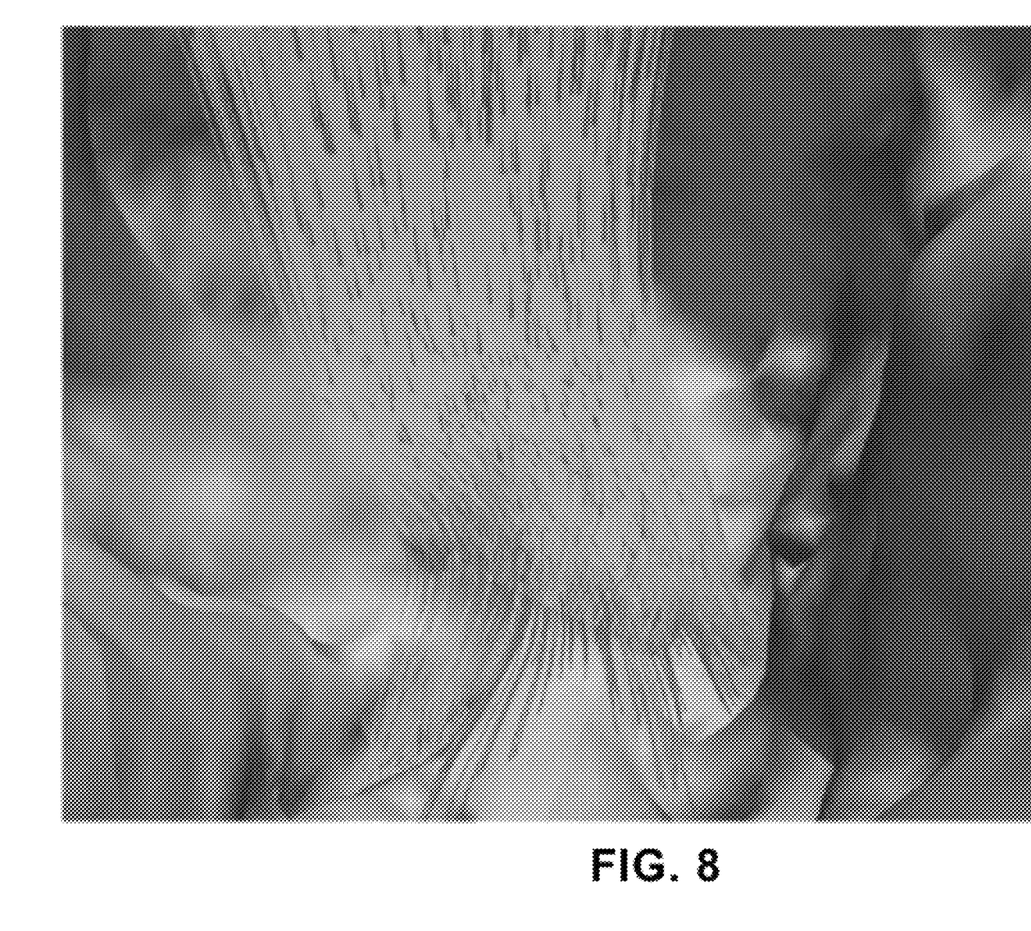
FIG. 8 illustrates blood flow streamlines during systole at the apex, against the trabeculae resuling from modeling of fluid flow through the model of the heart illustrated in FIG. 3

Finally, several streamline visualizations were generated, as seen in FIGS. 1, 7, and 8. The color at a point within a streamline is chosen in the same way as the cones described above—red streamlines signify fast moving blood, while blue streamlines represent lower speeds. In order to disambiguate direction, a small number of arrows within the streamline are added to point the way it is flowing.

Results and Discussion

Figure 6:
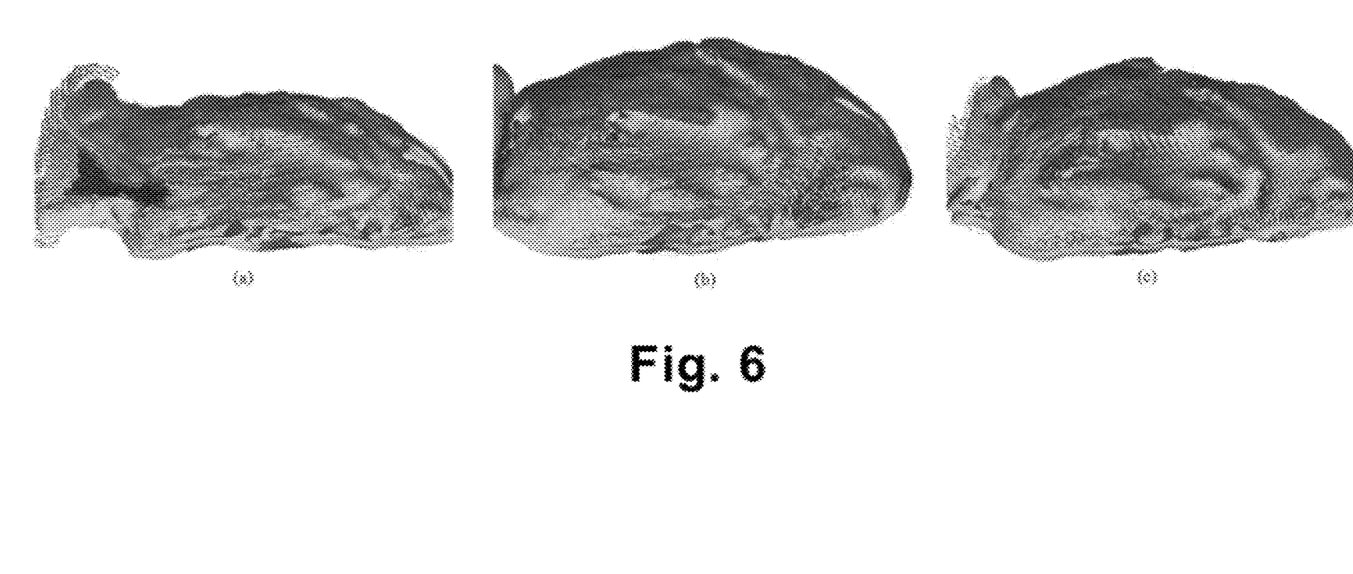
FIG. 6a illustrates a simulation of the blood flow at the beginning of diastole wherein the velocity field is plotted near the walls of the heart
FIG. 6b is the illustration of FIG. 6a illustrating the heart immediately before systole.
FIG. 6c is the illustration of FIG. 6d during systole.

The visualizations of the blood flow through the healthy heart then are analyzed. FIG. 6 contains three cross-sectional visualizations at different stages of the cardiac cycle. Here, the complex structure of the heart walls that has been passed to the fluid simulator is seen. The visualizations also can show the interactions between the trabeculae and the blood flow, which is far more accurate than previous attempts at cardiac blood flow simulation, whose methods have all assumed smooth heart walls. To the best of our knowledge, the level of detail achieved in the model and simulation has not been possible before.

In FIG. 6(a), the flow field visualization at the beginning of diastole is seen. FIG. 6(b) then shows the flow field shortly before systole, as the blood continues to rapidly circulate within the trabeculae. Finally, FIG. 6(c) visualizes the heart during systole, as blood is being ejected. Here, blood is shown to be squeezed out of trabeculae as the heart tissue contracts, shirking the gaps.

The streamline visualizations provide further evidence of the trabeculae-blood interaction. FIG. 7, taken during diastole, demonstrates how the complex surface causes the flow to become more chaotic as the blood approaches the apex, filling the empty spaces. The development of many small vortices around the trabeculae is clearly seen, which previous methods of cardiac blood flow simulation have not even attempted to capture. Then, in FIG. 8, during systole, rather than simply flowing directly towards the aortic valve as older methods with simpler meshes have suggested, the blood is forcefully expelled out of the trabeculae All of these visualizations show that the blood is continuously moving in and out of the trabeculae during the cardiac cycle, suggesting that it is constantly being flushed out of these spaces. It was hypothesized that in cases of hypokinesis, or other heart disorders, the blood may not be fully squeezed out of the trabeculae, leaving it trapped and stagnant. This could lead to the formation of thrombi and thus increased risk of stroke.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein and or referenced below are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application and are incorporated herein by reference in their entirety.

Nothing herein is to be construed as an admission that the present invention is not entitled to antedate such publication by virtue of prior invention. Further, the dates of publication provided may be different from the actual publication dates which may need to be independently confirmed.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

REFERENCES

CHEN, T., METAXAS, D. N., AND AXEL, L. 2004. 3D cardiac anatomy reconstruction using high resolution ctdata. In MICCAI (1), 411-418.

DE ZLICOURT, D., G E, L, WANG, C, SOTIROPOULOS, F., GILMANOV, A., AND YOGANATHAN, A. 2009. Flow simulations in arbitrarily complex cardiovascular anatomies—an unstructured cartesian grid approach. Computers & Fluids 38, 9, 1749-1762.

ENRIGHT, D., MARSCHNER, S., AND FEDKIW, R. 2002. Animation and rendering of complex water surfaces. ACM Trans. Graph. 21, 3, 736-744.

FOSTER, N., AND FEDKIW, R. 2001. Practical animation of liquids. In SIGGRAPH '01: Proceedings of the 28th annual conference on Computer graphics and interactive techniques, ACM, New York, N.Y., USA, 23-30.

FOSTER, N., AND METAXAS, D. 1996. Realistic animation of liquids. Graph. Models Image Process. 58 (September), 471-483.

GILMANOV, A., AND SOTIROPOULOS, F. 2005. A hybrid cartesian/immersed boundary method for simulating flows with 3d, geometrically complex, moving bodies. J. Comput. Phys. 207, 2, 457-492.

The visible human project, http://www.nlm.nih.gov.

JONES, T., AND METAXAS, D. 1998. Patient-specific analysis of left ventricular blood flow. 156-166. 10.1007/BFb0056198.

LORENZ, C, AND VON BERG, J. 2006. A comprehensive shape model of the heart. Medical Image Analysis 10, 4, 657-670.

MCQUEEN D., P. C. 2000. A three-dimensional computer model of the human heart for studying cardiac fluid dynamics. 34(1).

MIHALEF, V., METAXAS, D., AND SUSSMAN, M. 2007. Textured liquids based on the marker level set. Comput. Graph. Forum 26, 3, 457-466.

MIHALEF, V., KADIOGLU, S., SUSSMAN, M., METAXAS, D., AND HURMUSIADIS, V. 2008. Interaction of two-phase flow with animated models. Graph. Models 70, 3, 33-42.

MIHALEF, V., METAXAS, D., SUSSMAN, M., HURMUSIADIS. V., AND AXEL, L. 2009. Atrioventricular blood flow simulation based on patient-specific data. In FIMH '09: Proceedings of the 5th International Conference on Functional Imaging and Modeling of the Heart, Springer-Verlag, Berlin, Heidelberg, 386-395.

MIHALEF, V., IONASEC, R., WANG, Y., ZHENG, Y., GEORGESCU, B., AND COMANICIU, D. 2010. Patient-specific modeling of left heart anatomy, dynamics and hemodynamics from high resolution 4d ct. In ISBI'10: Proceedings of the 2010 IEEE international conference on Biomedical imaging, IEEE Press, Piscataway, N.J., USA, 504-507.

Q. LONG, R. M., G. Z. YANG, P. J. K., AND D. N. FIRMIN, X. Y. 2003. The influence of inflow boundary conditions on intra left ventricle flow predictions. 125, 922927.

SABER N., WOOD N., G. A. D. M. R. Y. G. Z. C. C. G. P. F. D. 2003. Progress towards patient-specific computational flow modeling of the left heart via combination of magnetic resonance imaging with computational fluid dynamics. 31(1), 42-52.

SHEN, D., AND DAVATZIKOS, C. 2000. Adaptive-focus statistical shape model for segmentation of 3D MR structures. MICCAI, 206-215.

SHEN, T., L I, H., QIAN, Z., AND HUANG, X. 2009. Active volume models for 3d medical image segmentation. In CVPR, 707-714.

SUSSMAN, M. 2005. A parallelized, adaptive algorithm for multiphase flows in general geometries. Comput. Struct. 83, 6-7, 435-444.

VON BERG, J., AND LORENZ, C. 2005. Multi-surface cardiac modeling, segmentation, and tracking. In FIMH. 1-11.

YOKOI, K., XIAO, F., LIU, H., AND FUKASAKU, K. 2005. Three dimensional numerical simulation of flows with complex geometries in a regular cartesian grid and its application to blood flow in cerebral artery with multiple aneurysms. Journal of Computational Physics 202, 1, 1-19.

ZHENG, Y., BARBU, A., GEORGESCU, B., SCHEUERING, M., AND COMANICIU, D. 2008. Four-chamber heart modeling and automatic segmentation for 3D cardiac CT volumes using marginal space learning and steerable features. TMI 27, 11, 1668-1681.

ZHU, S., LEE, T., AND YUILLE, A. 1995. Region competition:unifying snakes, region growing, energy/Bayes/MDL for multiband image segmentation. In ICCV, 416-423.

What is claimed is:

1. A method for producing a simulation of subject-specific blood flow of a heart in a subject, the method comprising:
   (a) scanning an endocardial surface of the heart in the subject, utilizing a diagnostic imaging system, to obtain a computed tomography (CT) image of the endocardial surface of the heart, wherein the scanning captures a complex and detailed structure of heart walls and trabeculae;
   (b) decimating a mesh of the computed tomography image obtained from step (a) utilizing a computing device to a size sufficient to capture fine details of the heart, wherein the decimation allows collapse of one vertex into one of its neighbors;
   (c) performing detail-preserving smoothing of the mesh from step (b), utilizing a computing device, wherein the smoothing is restricted to a tangential direction; and
   (d) remeshing a triangular mesh from step (c) with an incremental isotropic remeshing technique, utilizing a computing device, thereby producing the simulation of the subject-specific blood flow of the heart, wherein a target edge length is set to be a mean of a current edge length.

2. The method according to claim 1, wherein the mesh in step (b) is decimated to about 20,000 vertices.

3. The method according to claim 1, wherein the detail-preserving smoothing of step (c) preserves high quality meshes without losing structural detail.

4. The method according to claim 1, wherein during the incremental isotropic remeshing process in step (d):

(i) edges longer than the target edge length are split until all edges are shorter than the target edge length;
(ii) shorter edges are collapsed if collapsing does not result in new edges longer than a higher threshold;
(iii) edges are flipped to equal valences;
(iv) vertices are moved to new positions to obtain regular triangle meshes; and
(v) vertices are projected back to original surfaces to keep a shape unchanged.

5. A method for producing a simulation of subject-specific blood flow of a heart in a subject, the method comprising:
(a) scanning a patient's heart to obtain image data representative of an endocardial surface of the heart, including details of trabeculae;
(b) processing the image data to create a model of at least a portion of the patient's heart, wherein the model comprises a mesh comprising a plurality of geometric elements having edges;
(c) applying an isotropic remeshing technique to remesh the model so that edges of the geometric elements have approximately the same length;
(d) remeshing a triangular mesh from step (c) with an incremental isotropic remeshing technique, utilizing a computing device, thereby producing the simulation of the subject-specific blood flow of the heart, wherein a target edge length is set to be a mean of a current edge length;
(e) using shape features of the model as boundary conditions.

6. The method of claim 5 wherein the step of scanning a patient comprises scanning a patient to produce a series of computed tomography images.

7. The method of claim 5 comprising the step of decimating the mesh, wherein the decimation includes collapsing of vertices of the geometric elements into vertices of neighboring geometric elements.

8. The method of claim 5 wherein the step of applying an isotropic remeshing technique comprises selectively collapsing edges shorter than a threshold and moving vertices of the geometric elements so that the geometric elements are regular.

9. A method for producing a simulation of subject-specific blood flow of a heart in a patient, the method comprising the steps of:
creating a patient-specific three-dimensional heart model from image data obtained by scanning the patient, wherein the heart model includes pre-defined heart valve models and wherein the image data obtained by scanning the patient illustrates the timing of opening and closing of the patient's heart valves during a cardiac cycle;
correlating the timing of opening and closing of the valve models during a cardiac cycle with the timing of opening and closing of the valve models during a cardiac image data obtained by scanning the patient;
deforming the valve models as the heart model deforms during the cardiac cycle, wherein the step of deforming the valve models comprises deforming parts of the valve models that are connected to the heart model as the heart model deforms during the cardiac cycle;
using a finite differences process to discretize a domain that includes portions of the heart model; and
solving Navier Stokes equations throughout the domain so that one-way momentum transfer between the heart model and the blood is enforced.

10. The method of claim 9 wherein the step of deforming the valve models comprises interpolating movement of the valve models between frames in which the valve models have been correlated with the patient image data as being in the opened or closed position.

11. The method of claim 9 comprising the step of embedding the heart model in a computational mesh of a plurality of cells and wherein the step of solving Navier-Stokes equations comprises the step of applying a staggered grid across the domain and explicitly solving for three components of velocity at the cell faces.

12. The method of claim 11 wherein the mesh and its velocity are rasterized onto the Eulerian grid as a marker level set and the marker level set and the velocity are used to impose boundary conditions during the step of solving Navier Stokes equations.

13. The method of claim 12 wherein markers are placed on boundaries and are used to correct the level set at every time step.

14. A method for producing a simulation of subject-specific blood flow of a heart in a subject from a plurality of three-dimensional images of a heart of the subject representing a cardiac cycle for the subject, the method comprising the steps of:
generating an initial model of the heart of the subject, wherein the step of generating an initial model comprises the steps of:
segmenting a first image of the plurality of three-dimensional images;
generating a model mesh from the first segmented image using isosurface detection;
segmenting the plurality of three-dimensional images, other than the first image, by deforming the initial model toward boundaries, wherein for each of the plurality of three-dimensional images, deforming the initial model toward boundaries, comprises the step of:
minimizing an energy function to drag the model toward the boundaries and maintain the model unchanged during deformation, wherein the energy function includes an external energy and a model energy, wherein the external energy is derived from the image so that it is smaller at the boundaries, and a model energy, which reflects differences between the original model and the deformed model;
generating a model mesh from each of the plurality of three-dimensional images other that the first image, wherein the step of generating a model mesh from each of the plurality of three-dimensional images is based on the step of segmenting the plurality of three-dimensional images;
wherein each of the model meshes include detailed structure of the heart walls and trabeculae.

15. The method of claim 14 wherein the step of minimizing an energy function comprises the step of using a greedy algorithm to minimize the energy function.

16. The method of claim 15 wherein the step of using a greedy algorithm comprises an iterative process wherein during each iteration, the external energy is minimized and then the internal energy is minimized.

17. The method of claim 14 wherein the step of generating model mesh from the first three-dimensional image, comprises the step of decimating a mesh of the first image by allowing one vertex of an element in the mesh to collapse into one of its neighbors.

18. The method of claim 17 comprising the step of remeshing a triangular mesh after the step of decimating the mesh, wherein the step of remeshing comprises the step of using an incremental isotropic remeshing technique, wherein a target edge length is set to be a mean of a current edge length.

19. The method of claim 17 comprising the step of performing detail-preserving smoothing of the mesh after the step of decimating the mesh, wherein the smoothing is restricted to a tangential direction.

20. A method for producing a simulation of subject-specific blood flow of a heart in a subject from a plurality of three-dimensional images of a heart of the subject representing a cardiac cycle for the subject, the method comprising the steps of:
   obtaining an initial segmentation of a first of the images;
   generating an initial 3D frame mesh based on the step of obtaining an initial segmentation, wherein the step of generating an initial 3D frame mesh comprises generating the initial 3D mesh model as an isosurface of the initial segmentation;
   applying geometric processing to the initial 3D mesh model to provide a smooth and regular initial model mesh with a number of vertices;
   deforming the initial model toward boundaries on the other images to generate a series of model meshes representing the cardiac cycle of the subject, wherein during the step of generating a series of model meshes, the topology of the model is kept unchanged.

21. The method of claim 20 wherein a one-to-one correspondence is maintained between each of the series of model meshes and the plurality of three-dimensional images to facilitate simulating subject-specific blood flow.

\* \* \* \* \*